United States Patent [19]

Changaris

[11] Patent Number: 5,275,155
[45] Date of Patent: Jan. 4, 1994

[54] APPARATUS TO PROVIDE PULSES OF LIGHT

[76] Inventor: David G. Changaris, 1132 Rostrevor Cir., Louisville, Ky. 40205

[21] Appl. No.: 819,116

[22] Filed: Jan. 10, 1992

Related U.S. Application Data

[63] Continuation-in-part of Ser. No. 675,689, Mar. 27, 1991.

[51] Int. Cl.⁵ .............................................. A61N 5/06
[52] U.S. Cl. .................................. 607/94; 250/493.1;
250/498.1; 250/504 R; 359/227; 359/233;
359/235; 606/2
[58] Field of Search ............... 128/362, 371, 372, 373,
128/374, 375, 376, 377, 378, 395, 396; 606/2,
10, 13, 17; 340/815.15, 815.17, 815.26;
250/493.1, 494.1, 496.1, 497.1, 498.1, 503.1,
504; 359/227, 230, 232, 233, 234, 235, 236, 889

[56] References Cited

U.S. PATENT DOCUMENTS

| | | | |
|---|---|---|---|
| 897,823 | 9/1908 | Endall | 340/815.17 |
| 1,670,816 | 5/1928 | Lewis | 340/815.15 |
| 1,877,566 | 9/1932 | Elsey et al. | 359/233 |
| 2,347,672 | 5/1944 | Dircksen et al. | 250/504 R |
| 2,557,219 | 6/1951 | Flint et al. | 359/233 |
| 2,761,959 | 9/1956 | Kunins | 359/233 |
| 3,042,046 | 7/1962 | Willems | 128/372 |
| 3,990,787 | 11/1976 | Modert | 359/233 |
| 4,025,795 | 5/1977 | Lackore et al. | 250/504 R |
| 4,592,083 | 5/1986 | O'Brien | 250/498.1 |
| 5,046,494 | 9/1991 | Searfoss et al. | 128/395 |

*Primary Examiner*—Jessica J. Harrison
*Attorney, Agent, or Firm*—Middleton & Reutlinger

[57] ABSTRACT

A mechanical apparatus to provide pulses of light for tanning. One embodiment of the apparatus comprises a light source radiating light; a hollow cylinder having an inner and an outer cylindrical surface and an axis, the hollow cylinder having at least one opening through the inner to the outer cylindrical surface, the light source being inside the hollow cylinder, at least some of the light radiating from the light source passing through the at least one opening in the hollow cylinder; an apparatus to axially rotate the hollow cylinder; and, a surface having an opening therethrough. As the hollow cylinder is axially rotated, at least some of the light radiating from the light source passing through the at least one opening in the hollow cylinder will come into light communication with the opening in the surface and pass therethrough, thereby creating a pulse of light. Another embodiment incorporates at least two counter rotating cylinders which are coaxially aligned around a light source. Further, devices employing a plurality of side by side cylinder combinations is included. These combinations rotate so that pulses of light are simultaneously radiated from each cylinder. The cylinders can be rotated by a motor or by an air turbine.

7 Claims, 6 Drawing Sheets

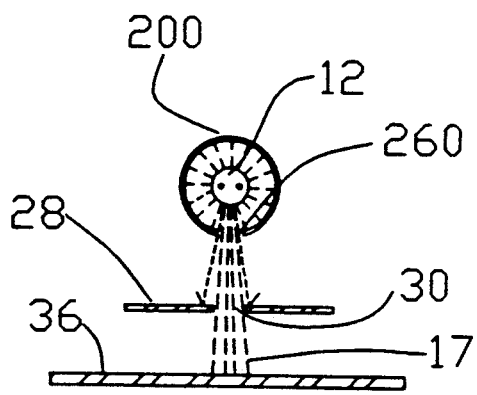 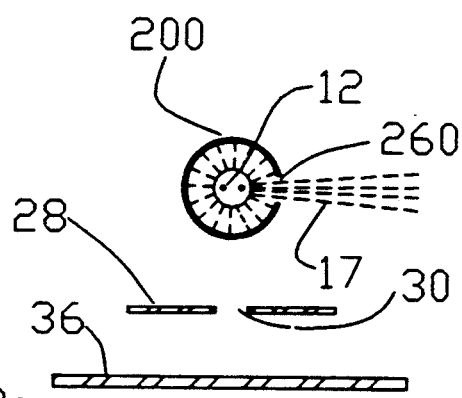
Fig. 3a
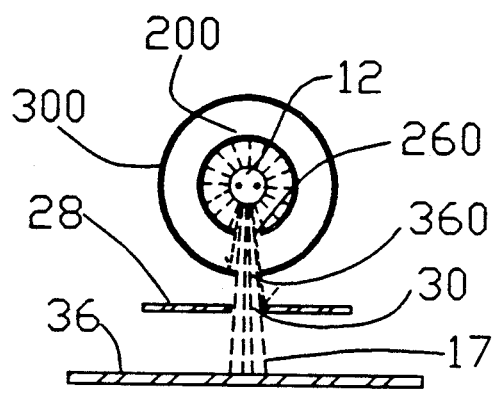 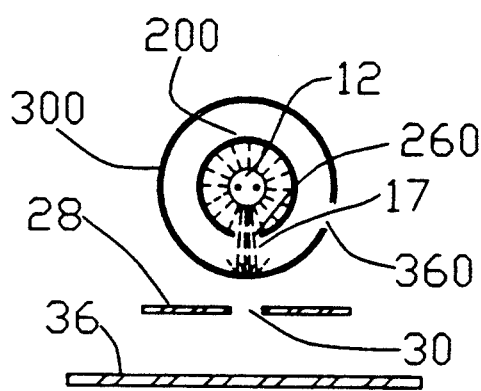
Fig. 3b
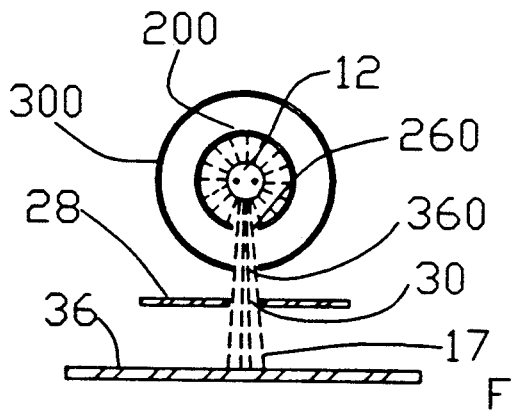 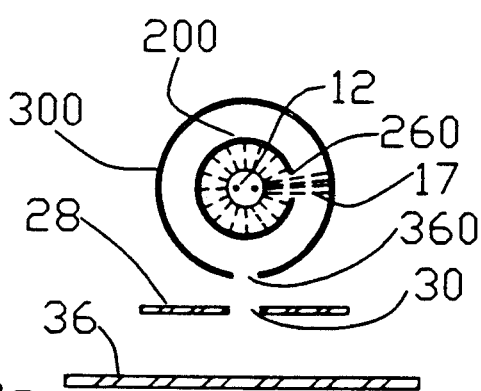
Fig. 3c
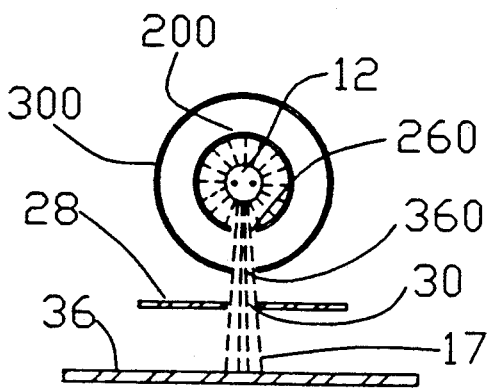 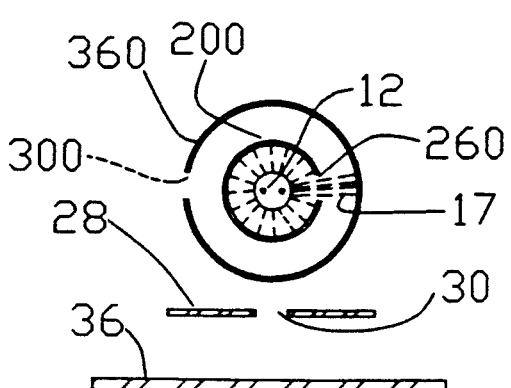
Fig. 3d

APPARATUS TO PROVIDE PULSES OF LIGHT

This is a continuation-in-part application of my U.S. patent application Ser. No. 07/675,689, filed Mar. 27, 1991 pending, for a Method of Inducing Tanning or DNA Repair by Pulsed Light and Apparatus to Effect Same, which is incorporated herein by reference, and hereinafter referred to as the "parent application".

BACKGROUND OF THE INVENTION (a) Field of the Invention

The present invention relates to an apparatus to provide pulses of light. In my parent application, I disclosed a mechanically-pulsed irradiation generation apparatus having a light source and at least one rotating cylinder having slits which allowed a discrete pulse of light to pass therethrough when in proper alignment. In my parent application, I further teach placing the cylinder adjacent to the light source. This configuration results in the majority of the light being wasted when a circumferential omnidirectional radiating light source is employed, as the slits pass only that amount of light radiated toward them. Therefore, I have now invented a much more efficient apparatus to provide the mechanically-pulsed light. This is accomplished by placing at least one hollow cylinder having at least one opening through the cylindrical surface around the light source, and that is the focus of this continuation-in-part application.

(b) Description of the Prior Art

The prior art identified in my parent application is herein incorporated by reference. I have discovered no additional art relevant to my present invention.

SUMMARY OF THE INVENTION

The present invention is for an improved apparatus to provide discrete pulses of light. In the parent application, I taught that "by subjecting the skin to very short, discrete pulses of UV energy, it is possible to effect an inducement of the melanocytes to produce pigmentation changes equivalent to those produced by continuous UV irradiation sources, but without manifesting tissue injury...." I further taught that "exposure to pulsed light will induce tanning."

Discrete pulses of light can be provided by mechanical or electrical means. In my parent application, I disclosed a mechanically-pulsed irradiation generation apparatus having a light source and at least one rotating cylinder having slits which allowed a pulse of light to pass therethrough when in proper alignment. In my parent application, I further teach placing the cylinder adjacent to the light source. However, experience has shown that arrangement results in the majority of the light being wasted, as the light source employed circumferentially radiates light omnidirectionally and the slits pass only that amount of light radiated toward them. Therefore, I have now invented a much more efficient apparatus to provide the mechanically-pulsed light. This is accomplished by placing at least one hollow cylinder having at least one opening through the cylinder's surface around the light source.

More particularly, the present invention comprises an apparatus to provide discrete pulses of light, wherein a rotatable cylinder having at least one opening in its cylindrical surface is placed around a light source. Depending upon the size of the at least one opening, as the cylinder is rotated, light is transmitted from the light source out the at least one opening, thereby pulsing a fixed location outside the cylinder. For example, based on geometric relationships between the rotatable cylinder and the at least one opening and the rate of rotation of the cylinder, my apparatus will generate these discrete pulses of light having a pulse duration in the microsecond to centisecond range. The cylinder may be rotated by direct drive means for the millisecond pulses or air turbines to effect microsecond pulses.

Even more particularly, the present invention comprises an apparatus to provide discrete pulses of light, comprising: a light source radiating light; a hollow cylinder having an inner and an outer cylindrical surface and an axis, said hollow cylinder having at least one opening through said inner to said outer cylindrical surface, said light source being inside said hollow cylinder, at least some of said light irradiating from said light source passing through said at least one opening in said hollow cylinder; means to axially rotate said hollow cylinder; and, a surface having an opening therethrough, wherein as said hollow cylinder is axially rotated, at least some of said at least some of said light irradiating from said light source passing through said at least one opening in said hollow cylinder will come into light communication with said opening in said surface and pass therethrough, thereby creating a pulse of light.

Finally, in the present invention a plurality of light sources are each placed inside a first hollow cylinder having at least one opening in its cylindrical surface. The first cylinders are each placed inside a second hollow cylinder also having at least one opening in its cylindrical surface. The openings in the first hollow cylinders are in parallel alignment, as are the openings in the second hollow cylinders. A means to axially rotate the cylinders rotates the first hollow cylinders in one direction and the second hollow cylinders in the opposite direction. The cylinders are rotated at the same number of revolutions per unit time. When each light source is in light communication with its respective at least one opening in the first hollow first cylinder and its respective at least one opening in the second hollow cylinder, a pulse of light is simultaneously transmitted from each light source in a specific direction.

BRIEF DESCRIPTION OF THE DRAWINGS

A better understanding of the present invention will be had upon reference to the following description in conjunction with the accompanying drawings, wherein:

FIGS. 3a–3d show selected light radiation patterns for the apparatuses shown in FIGS. 1 and 2;

DETAILED DESCRIPTION OF THE PREFERRED EMBODIMENT

Figure 1:
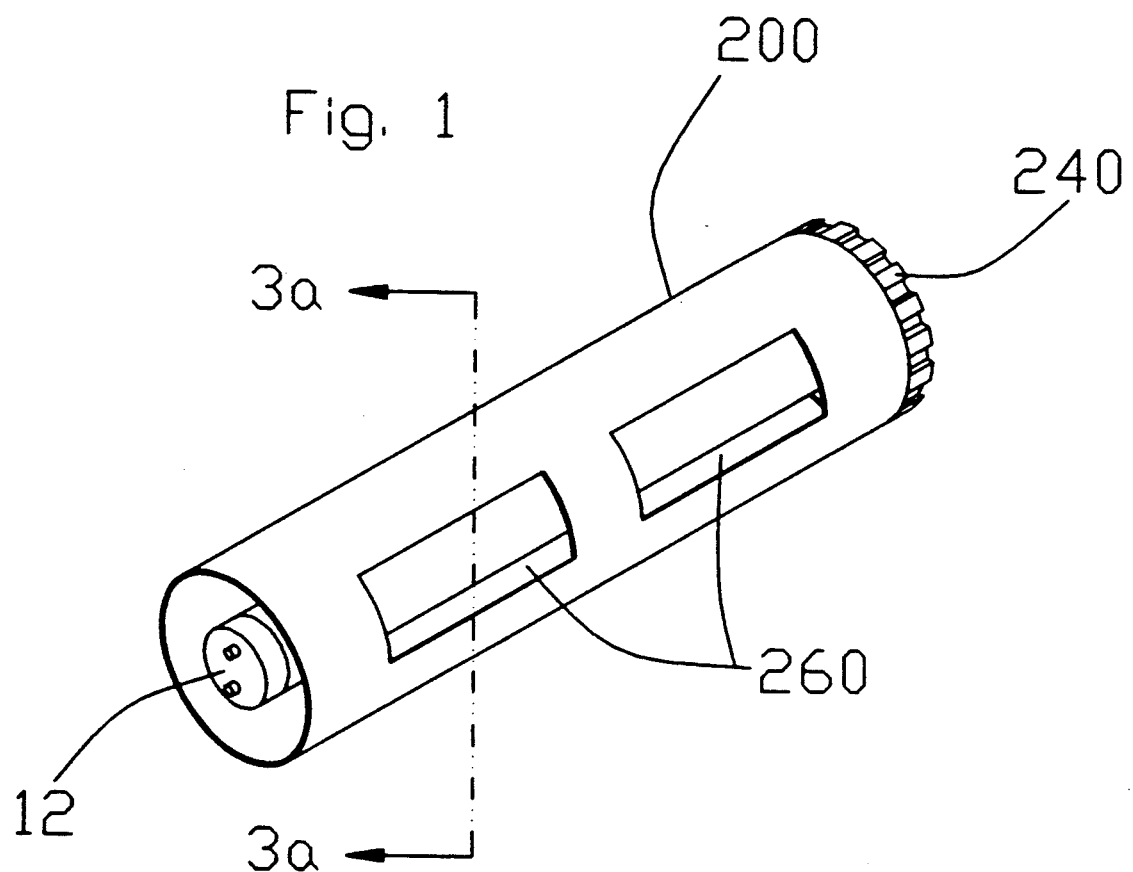
FIG. 1 shows a perspective view of a light source inside a hollow cylinder having openings therethrough of one embodiment of the present invention.
Figure 2:
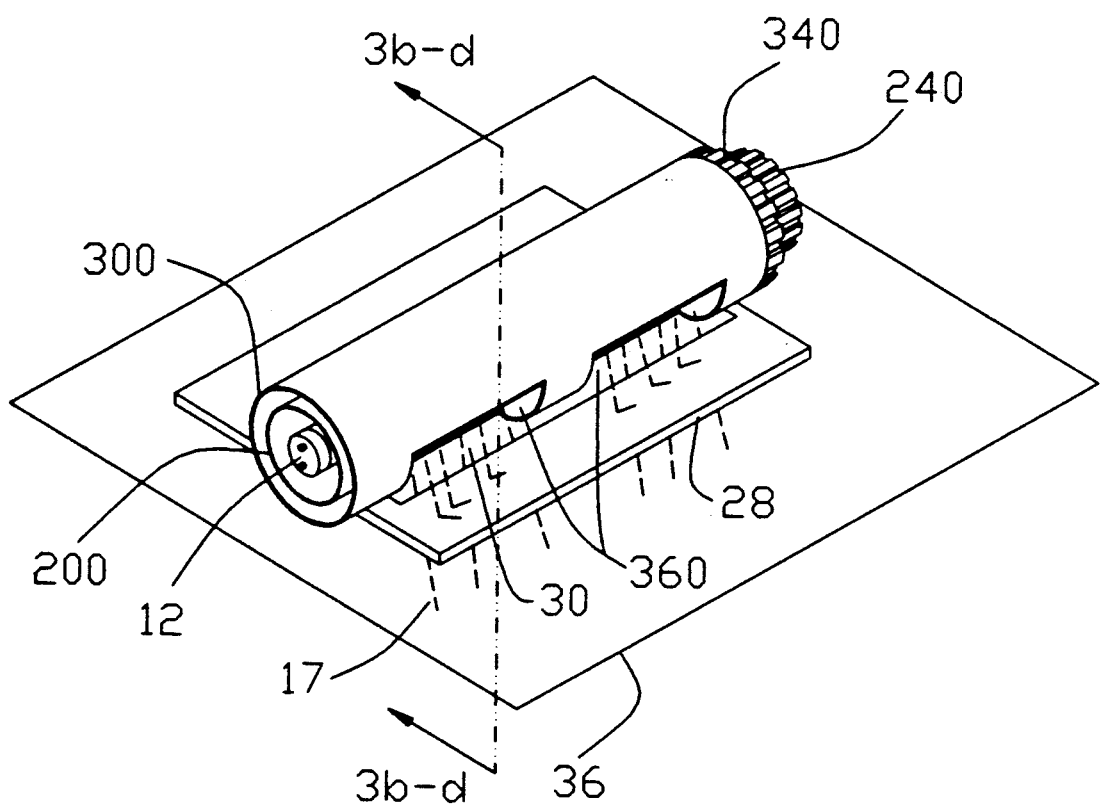
FIG. 2 shows a perspective view of a light source inside a pair of hollow cylinders having openings therethrough of another embodiment of the present invention.

The figures show different embodiments of the present invention. FIG. 1 shows an circumferentially omnidirectional light source inside one hollow cylinder having openings therethrough of one embodiment of the present invention. FIG. 2 shows an circumferentially omnidirectional light source inside a pair of hollow cylinders having openings therethrough of another embodiment of the present invention. FIG. 3 shows selected light radiation patterns for the apparatuses shown in FIGS. 1 and 2. FIG. 4 shows a top and bottom view of one embodiment of the present invention incorporating a plurality of light sources, each inside one hollow cylinder. FIG. 5 shows one means to axially rotate a plurality of single cylinders and another means to axially rotate a plurality of inner and outer cylinders in opposite directions which could be used with the present invention. FIG. 6 shows how fins could be added to a cylinder to utilize air turbine technology to rotate the cylinder. For tanning, I believe that the inner and outer cylinder embodiment, such as shown in FIG. 2, is preferable, as it is desirable to only radiate light pulses in the direction(s) desired.

With reference now to FIG. 1, a light source 12 is shown inside a first hollow cylinder 200 having two openings 260 in the cylindrical surface. As will be explained later, sprockets 240 located at one end of cylinder 200 will be used to rotate cylinder 200 about its axis. In FIG. 2, the light source 12 and the first hollow cylinder 200 have been inserted into a second hollow cylinder 300. First cylinder 200 and second cylinder 300 are in coaxial alignment. The second cylinder 300 also has two openings 360 in its cylindrical surface. As shown in FIG. 2, first hollow cylinder 200 has an axial length greater than that of second hollow cylinder 300. The end of cylinder 200 having sprockets 240 extends axially outside the end of cylinder 300 having sprockets 340. As will be explained later, sprockets 240 and 340 will be used to rotate cylinder 200 in one direction about its axis and cylinder 300 in the opposite direction about its axis.

FIG. 2 also includes filter block or surface 28 having a slot or opening 30 therethrough. When light source 12, openings 260 in first cylinder 200, openings 360 in second cylinder 300, and opening 30 are in light communication, light from light source 12 passes therethrough. When one or both of first 200 and second 300 cylinders rotate, the alignment of openings 260, 360, and 30 is such that light passing through opening 30 from light source 12 toward surface 36 is in the form of a light pulse 17.

FIG. 3a shows a two-dimensional cross-section along the lines 3a of FIG. 1, with the addition of surface 28 having opening 30, surface 36, and light beam 17. With light source 12 continuously circumferentially radiating light omnidirectionally, the rotation of cylinder 200 causes a "lighthouse effect." Light 17 passing through opening 260 will rotate around the axis of cylinder 200 causing a pulse of light to pass through opening 30 and irradiate a fixed location on surface 36 for each rotation of cylinder 200. However, for example, because of the rate of revolution which will be used for tanning, a human eye would not detect this "lighthouse effect", but, instead, would sense continuous light.

Increasing the reflectivity of the inner cylindrical surface of cylinder 200 for the wavelength(s) of light 17 being radiated by omnidirectional light source 12 will cause more power per unit area to irradiate the fixed location on surface 36. In contrast, light source 12 can be constructed so that it only radiates light in the direction of the fixed location on surface 36 to be pulsed. There will then be no "lighthouse effect". Instead, rotating cylinder 200 will cause pulses of light to appear at the fixed location on surface 36 by having the inner cylindrical surface of cylinder 200 interrupt the light 17 radiating toward that fixed location. With this directional light source 12, the inner cylindrical surface of cylinder 200 may be made more absorptive to the wavelength(s) of light 17 to decrease undesired reflections.

FIGS. 3b–d show two-dimensional cross-section views along the lines 3b–d of FIG. 2. FIGS. 3b–d all show an circumferential omnidirectional radiating light source 12, a first cylinder 200 having opening 260, a second cylinder 300 having opening 360, a surface 28 having opening 30, a surface 36, and a light beam 17. In FIG. 3b, first cylinder 200 is stationary and second cylinder 300 rotates. In FIG. 3c, first cylinder 200 rotates and second cylinder 300 is stationary. In FIG. 3d, first cylinder 200 and second cylinder 300 rotate at the same number of revolutions per unit time, but in opposite directions. In all three of these configurations, one pulse 17 irradiates a location on surface 36 each time light source 12 and openings 260, 360, and 30 are in light communication. The rotational speed of the rotating one or both cylinders will determine the period "q". The geometric relationships between the size of the various openings and the cylinder dimensions, along with rotational speed will determine the length of time "x" when there is a pulse at surface 36. During the dark period "z" there is no pulse at surface 36. Therefore, as was disclosed in my parent application, "x+z=q". For example, I envision that in tanning, the dark period will be at least three times longer than the pulse period. However, depending on the application and exposure desired, this relationship will vary greatly.

As was discussed with FIG. 3a, increasing the reflectivity of the inner cylindrical surface of first cylinder 200 for the wavelength(s) of light 17 being radiated by circumferential omnidirectional light source 12 will cause more power per unit area to irradiate the location on surface 36. Further, depending on the geometry, it may be desirable for the inner cylindrical surface of first cylinder 200 to have parabolic shape to geometrically focus light 17 through opening 260.

Because the only time a pulse is desired is when light source 12 and openings 260, 360, and 30 are in light communication, the outer cylindrical surface of first cylinder 200 and both the inner and outer cylindrical surfaces of second cylinder 300 can be made absorptive to the wavelength(s) of light 17 being radiated by light source 12. Again, as was discussed with the single cylinder configuration of FIG. 3a, light source 12 can be constructed so that it only radiates light in the direction where light source 12 and openings 260, 360, and 30 are in light communication.

Figure 4A:
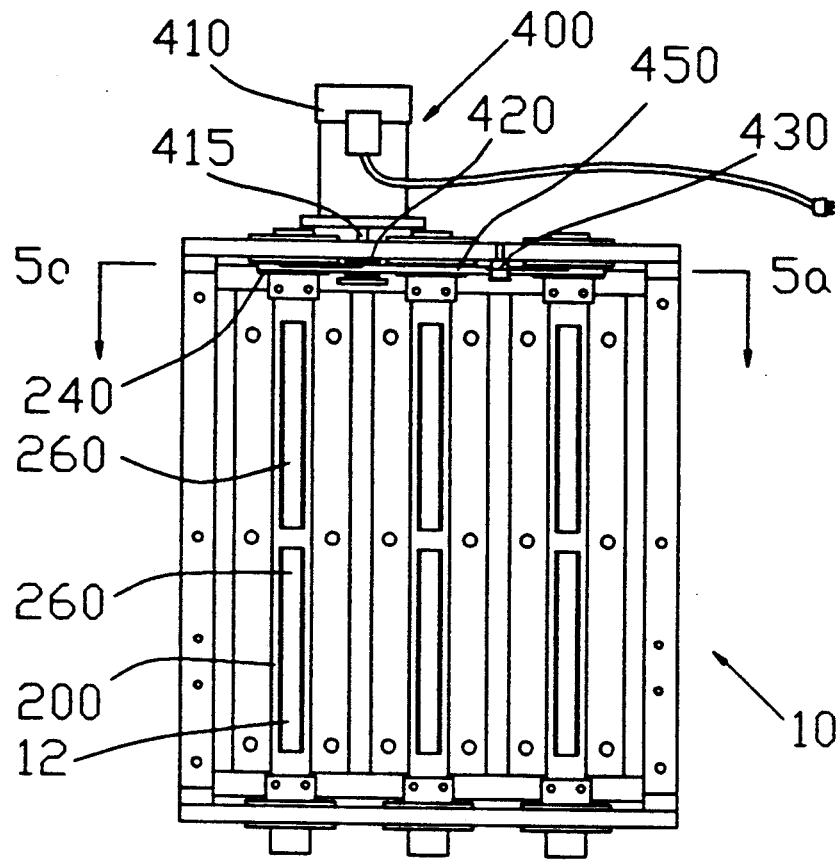
FIGS. 4a and 4b show a top and bottom view of one embodiment of the present invention incorporating a plurality of light sources.

FIG. 4a is a top view of an apparatus 10 to provide pulses of light. In operation, the top of apparatus 10 would have a protective cover installed. Apparatus 10 has three light sources 12 each contained in a hollow cylinder 200. Each cylinder 200 has two openings 260 through the cylindrical surface of cylinder 200. As shown, the two openings 260 in each cylinder 200 have a combined length which approximates the length of the light source 12 inside the cylinder 200. The openings 260 each have a width which approximates the diameter of the light source 12 inside the cylinder 200. Also, all openings 260 in all cylinders 200 are aligned in parallel, for example, all openings 260 are shown facing up. The three cylinders are shown spaced equally apart and parallel to each other. This spacing will be determined by how far away surface 36 to be irradiated by a pulse, shown in previous figures, is from apparatus 10 and the desired irradiation pattern on surface 36. For tanning, uniform power per unit area irradiation distribution is desired.

Figure 4B:
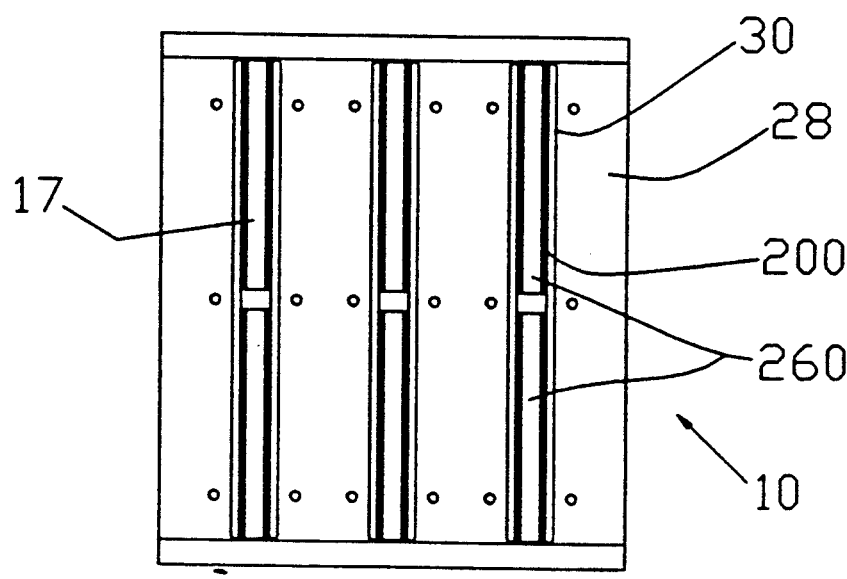

FIG. 4b shows a bottom view of apparatus 10 of FIG. 4a with cylinders 200 having been rotated 180 degrees from the position shown in FIG. 4a so that openings 260 now all face the bottom of apparatus 10. At the instant shown in FIG. 4b, a pulse of light 17 would be simultaneously transmitted from each light source 12 through openings 260 in each cylinder 200 and further through openings 30 in surface 28.

Figure 5A:
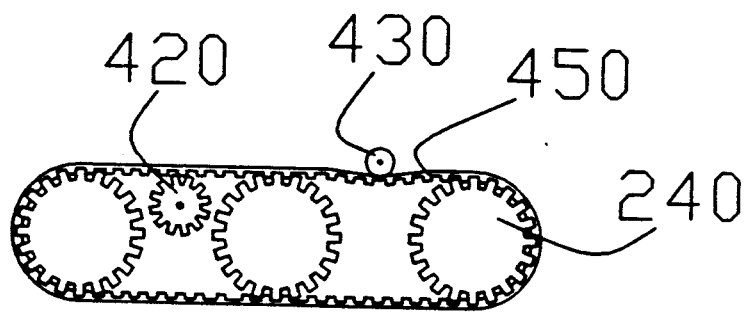
FIGS. 5a and 5b shows one means to axially rotate a plurality of single cylinders and another means to axially rotate a plurality of inner and outer cylinders in opposite directions, both means employing a motor, which could be used with the present invention; and, FIGS. 6a and 6b show alternative means to axially rotate cylinders using air turbine technology.

FIG. 4a also shows one typical rotation means 400. FIG. 5a shows a side view of means 400 along the lines 5a shown in FIG. 4a. With reference to both FIG. 4a and 5a, sprockets 240 at one end of each cylinder 200 are aligned in a plane. Means 400 is shown comprising a motor 410 having a shaft 415 connected to a sprocketed gear drive 420. A sprocketed endless conveyor 450 engages the appropriate sprockets 240 of each cylinder 200 and sprocketed gear drive 420. Conveyor tension means 430 maintains proper tension on sprocketed endless conveyor 450. As motor 410 rotates shaft 415 and thereby rotates sprocketed gear drive 420, sprocketed endless conveyor 450 rotates, thereby rotating cylinders 200.

Figure 5B:
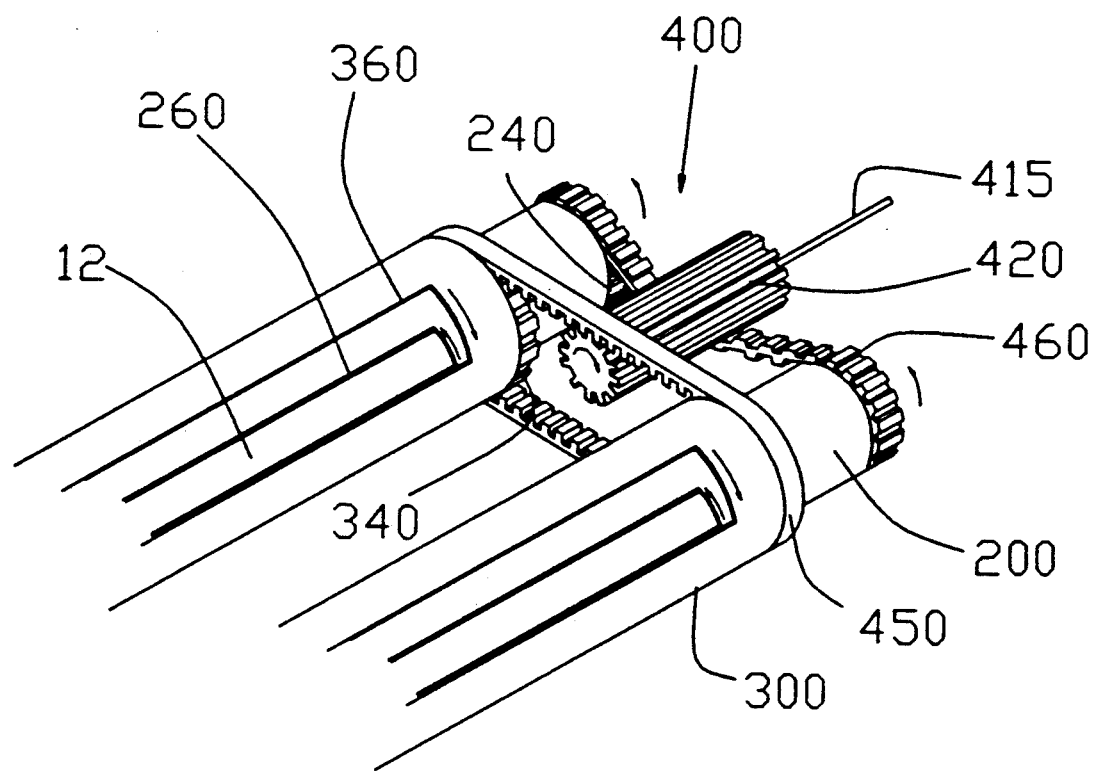

FIG. 5b shows how rotation means 400 could be used to rotate a pair of first hollow cylinders 200 axially in one direction and a pair of second hollow cylinders 300 axially in the opposite direction. Rotation means 400 comprises a motor (not shown) connected to shaft 415 which is connected to sprocketed gear drive 420. As with the three single cylinders 200 shown in FIGS. 4a and 5a, sprocketed endless conveyor 450 engages sprocketed gear drive 420. It also engages appropriate sprockets 340 of each second cylinder 300. A second sprocketed endless conveyor 460 having sprockets on both sides is used. Sprockets on one side of conveyor 460 engage appropriate sprockets 240 of each cylinder 200 and sprockets on the other side of conveyor 460 engage sprocketed gear drive 420. In this embodiment, conveyors 450 and 460 are sized to ensure proper rotational timing so that all cylinders 200 and all cylinders 300 rotate at the same number of revolutions per unit time. Openings 260 in all first cylinders 200 are in parallel, as are openings 360 in all second cylinders 300. This, along with the equal rotational speed of all cylinders 200 and 300 will ensure that light pulses 17 will simultaneously pass from each light source 12 through openings 260 and 360 and will always be directed to the same location with each rotation of cylinders 200 and 300.

In the alternative, instead of connecting a motor to shaft 415, a means to employ air turbine technology could be connected. Simply by connecting to shaft 415 a device having a plurality of fins and by having a compressed air source provide high speed air onto these fins, shaft 415 would rotate as above. Conveyors 450 and 460 would again act as timing belts to control rotation of the cylinders 200 and 300.

Figure 6A:
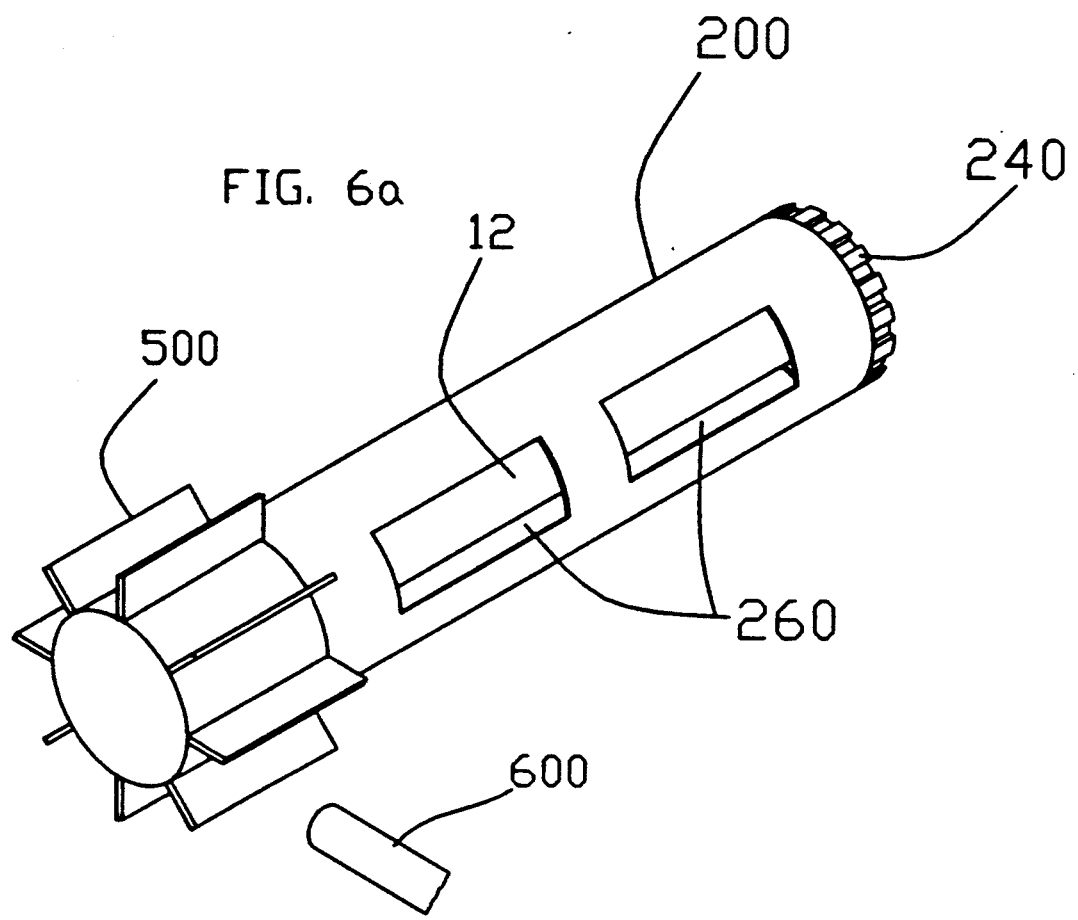
Figure 6B:
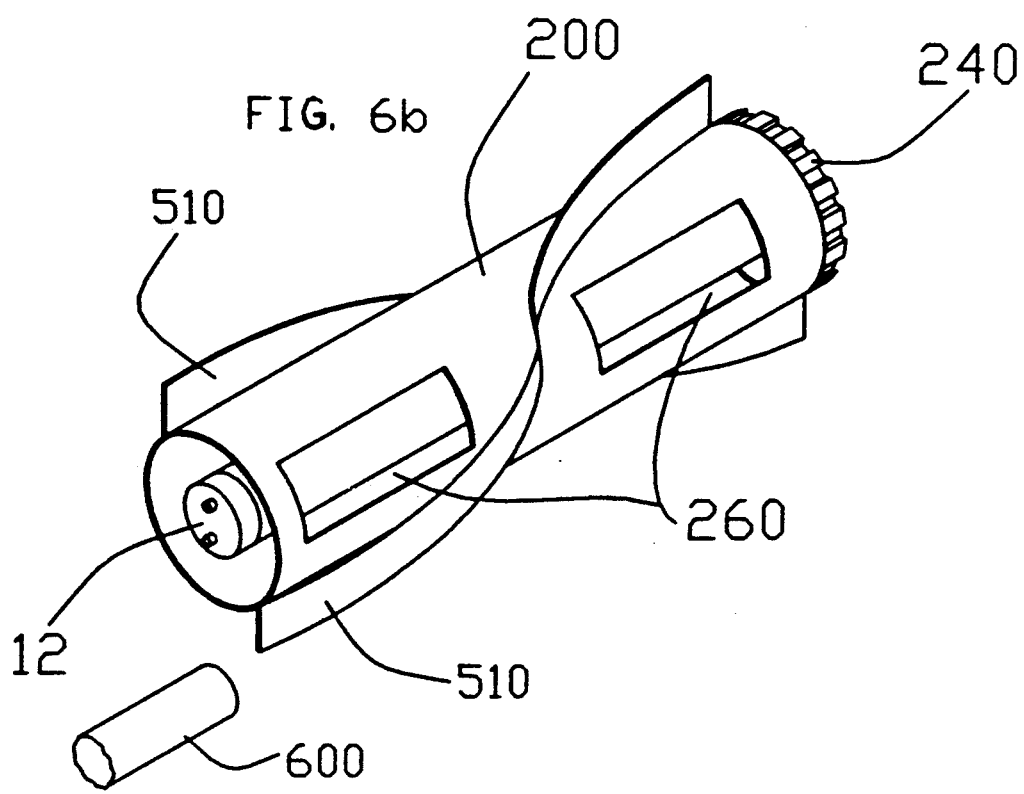

FIGS. 6a and 6b show alternatives to this which also employ air turbine technology. In FIG. 6a, fins 500 are added at the non-sprocketed end of cylinder 200 and compressed air is delivered onto fins 500 through nozzle 600 to rotate cylinder 200. Depending on the application, sprockets 240 can engage a conveyor, as previously described, to ensure that a plurality of cylinders will rotate with proper timing. FIG. 6b incorporates fins 510 which helically wrap around the outside surface of cylinder 200, positioned so as to not interfere with the light exiting openings 260. Placing cylinder 200 inside cylinder 300, as previously disclosed, and placing nozzle 600 so that air is blown between the outer surface of cylinder 200 and the inner surface of cylinder 300 will cause cylinder 200 to rotate. Again, sprockets 240 can be used to ensure proper timing if a plurality of cylinders is employed.

For applications involving a cylinder 200 coaxially aligned with cylinder 300, such as was described in FIG. 2, those skilled in the art can easily see how the fins 500 of FIG. 6a could be placed on both cylinders 200 and 300 and how air could be directed to have the cylinders 200 and 300 rotate in opposite directions. Also, for the fins 510 of FIG. 6b, the fins 510 of cylinder 200 and 510 of cylinder 300 would helix in opposite directions around the outside surface of their respective cylinders so that air would cause the cylinders to rotate in opposite directions. In this configuration, an outer sheath at least partway around the outside cylinder would be required to direct the air along the outside of this outside cylinder to cause it to rotate. The outside cylinder performs this "sheath" function for the inner cylinder.

The foregoing detailed description is given primarily for clearness of understanding and no unnecessary limitations are to be understood therefrom for modifications can be made by those skilled in the art upon reading this disclosure and may be made without departing from the spirit of the invention and scope of the appended claims.

What is claimed is:

1. An apparatus to provide pulses of light for tanning skin, comprising:
   a. an elongated light source radiating light for tanning;
   b. a hollow cylinder having an inner and an outer cylindrical surface and an axis, said hollow cylinder having at least one elongated rectangular-shaped opening through said inner to said outer cylindrical surface, said light source being inside said hollow cylinder, said light radiating from said light source passing through said at least one elongated rectangular-shaped opening in said hollow cylinder;
   c. means to axially rotate said hollow cylinder at a preselected rate of rotation; and,
   d. a surface having an elongated opening therethrough, said surface being adjacent to said hollow cylinder and parallel to said axis of said hollow cylinder, wherein as said hollow cylinder is axially rotated, a pulse of light is sensed at a preselected tanning location distance from said apparatus when said light radiating from said light source passing through said at least one elongated rectangular-shaped opening in said hollow cylinder comes into light communication with said elongated opening in said surface, wherein the continual axial rotation of said hollow cylinder causes a plurality of light pulses to be sensed at said preselected tanning location, and wherein said preselected rate of rotation is at a sufficient rate such that said plurality of pulses of light appear as continuous light to a human eye at said preselected tanning location.

2. The apparatus of claim 1, wherein said inner cylindrical surface is reflective.

3. The apparatus of claim 1, said means to axially rotate said hollow cylinder at a preselected rate of rotation including a motor.

4. The apparatus of claim 1, said means to axially rotate said hollow cylinder at a preselected rate of rotation including an air turbine means.

5. The apparatus of claim 6, wherein said pulse of light sensed at said preselected tanning location distant from said apparatus has a preselected power per unit area distribution, said distribution being uniform over a preselected area for tanning.

6. An apparatus to provide pulses of light for tanning skin, comprising:
   a. a plurality of elongated light sources, each light source radiating light for tanning;
   b. a plurality of parallel equally spaced hollow cylinders each having an inner and an outer cylindrical surface and an axis, each of said hollow cylinders having at least one elongated rectangular-shaped opening through said inner to said outer cylindrical surface, each of said light sources being inside one of said hollow cylinders, said light radiating from each of said light sources passing through said at least one elongated rectangular-shaped opening in said hollow cylinder surrounding said light source;
   c. means to axially rotate said plurality of hollow cylinders, said plurality of hollow cylinders being rotated in synchronization at a preselected rate of rotation; and,
   d. a surface having a plurality of elongated openings therethrough, said surface being adjacent to said plurality of said hollow cylinders and parallel to said axes of said plurality of hollow cylinders, wherein as said plurality of hollow cylinders are axially rotated, a pulse of light is sensed at a preselected tanning location distance from said apparatus when said light radiating from each of said light sources passing through said at least one elongated rectangular-shaped opening in said hollow cylinder surrounding said light source comes into light communication with one of said elongated openings in said surface, wherein the continual axial rotation of said plurality of hollow cylinders in synchronization causes a plurality of light pulses to be sensed at said preselected tanning location, and wherein said preselected rate of rotation is at a sufficient rate such that said plurality of pulses of light appear as continuous light to a human eye at said preselected tanning location.

7. The apparatus of claim 1, wherein said elongated light source is cylindrical-shaped having a diameter and said at least one elongated rectangular-shaped opening through said inner to said outer cylindrical surface and said elongated opening in said surface each have a width which approximates said diameter of said light source.

* * * * *